(12) United States Patent
Eustache et al.

(10) Patent No.: US 10,646,620 B2
(45) Date of Patent: May 12, 2020

(54) USE OF PEBA HAVING LONG BLOCKS FOR THE MANUFACTURE OF ALL OR PART OF A CATHETER

(71) Applicant: ARKEMA FRANCE, Colombes (FR)

(72) Inventors: René-Paul Eustache, Combon (FR); Frédéric Malet, Lyons (FR); Eric Gamache, Philadelphia, PA (US); Alejandra Reyna-Valencia, Evreux (FR); Damien Rauline, Saint-Quentin-des-Isles (FR)

(73) Assignee: ARKEMA FRANCE, Colombes (FR)

( * ) Notice: Subject to any disclaimer, the term of this patent is extended or adjusted under 35 U.S.C. 154(b) by 126 days.

(21) Appl. No.: 15/303,077

(22) PCT Filed: Apr. 13, 2015

(86) PCT No.: PCT/FR2015/050978
§ 371 (c)(1),
(2) Date: Oct. 10, 2016

(87) PCT Pub. No.: WO2015/155489
PCT Pub. Date: Oct. 15, 2015

(65) Prior Publication Data
US 2017/0232152 A1    Aug. 17, 2017

(30) Foreign Application Priority Data

Apr. 11, 2014   (FR) ..................... 14 53224

(51) Int. Cl.
*A61L 29/06* (2006.01)
*C08G 69/40* (2006.01)
(Continued)

(52) U.S. Cl.
CPC ............ *A61L 29/06* (2013.01); *A61L 29/049* (2013.01); *A61M 25/10* (2013.01);
(Continued)

(58) Field of Classification Search
CPC ............................... A61L 29/06; C08G 69/40
See application file for complete search history.

(56) References Cited

U.S. PATENT DOCUMENTS 4,873,296 A * 10/1989 Ciaperoni .............. C08G 69/40
525/434
6,406,457 B1 * 6/2002 Wang ..................... A61L 29/06
428/35.2

(Continued)

FOREIGN PATENT DOCUMENTS

EP    0 156 035 A2   10/1985
EP    0 613 919 A1    9/1994
(Continued)

OTHER PUBLICATIONS

Gert Burkhardt, et al., "Plastics Process, 1. Processing of Thermoplastics," Ullmann's Encyclopedia of Industrial Chemistry, vol. 29, pp. 155-193, published online 2011 (Year: 2011).*

(Continued)

*Primary Examiner* — Nicholas E Hill
(74) *Attorney, Agent, or Firm* — Thomas F. Roland

(57) ABSTRACT

A copolymer containing polyether blocks and polyamide blocks for manufacturing an inflatable catheter element, such as a catheter balloon, with improved bursting strength, in which said copolymer has the following characteristics: number-average molecular mass of the PE blocks greater than 500 g/mol, and number-average molecular mass of the PA blocks greater than 10 000 g/mol.

3 Claims, 1 Drawing Sheet

(51) Int. Cl.
*A61L 29/04* (2006.01)
*A61M 25/10* (2013.01)

(52) U.S. Cl.
CPC ......... *A61M 25/1029* (2013.01); *C08G 69/40* (2013.01); *A61M 2025/1084* (2013.01)

(56) References Cited

U.S. PATENT DOCUMENTS

| | | |
|---|---|---|
| 6,590,065 B1 | 7/2003 | Goldfinger |
| 2002/0018866 A1 | 2/2002 | Lee et al. |
| 2010/0312180 A1 | 12/2010 | Lorenz |
| 2011/0143014 A1* | 6/2011 | Stankus .................. A61F 2/958 427/2.14 |
| 2011/0288478 A1* | 11/2011 | Ehrenreich ..... A61M 25/10181 604/99.04 |

FOREIGN PATENT DOCUMENTS

| | | |
|---|---|---|
| EP | 1 482 011 A1 | 12/2004 |
| FR | 2 846 332 A1 | 4/2004 |
| JP | 2004-346274 A | 12/2004 |
| JP | 2004-352794 A | 12/2004 |
| WO | WO 99/13924 A | 3/1999 |
| WO | WO-9913924 A2 * | 3/1999 ............. A61L 29/06 |
| WO | WO 2009/062711 A1 | 5/2009 |

OTHER PUBLICATIONS

International Search Report (PCT/ISA/210) dated Jul. 7, 2015, by the European Patent Office as the International Searching Authority for International Application No. PCT/FR2015/050978.

Written Opinion (PCT/ISA/237) dated Jul. 7, 2015, by the European Patent Office as the International Searching Authority for International Application No. PCT/FR2015/050978.

* cited by examiner

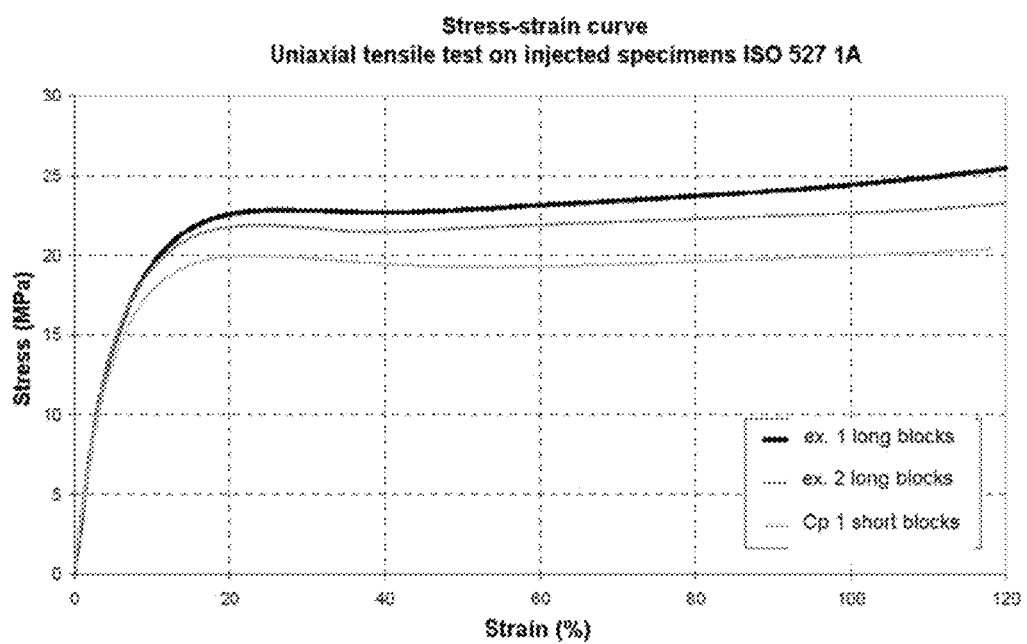

USE OF PEBA HAVING LONG BLOCKS FOR THE MANUFACTURE OF ALL OR PART OF A CATHETER

FIELD OF THE INVENTION

The present invention relates more particularly to an inflatable intravascular catheter element, such as a balloon or cuff.

The invention relates more particularly to the use of novel thermoplastic polymer compositions for manufacturing medical catheter balloons, which combine excellent "compliance" and bursting strength properties, as defined below. However, it may be envisaged to make another part or even all of the catheter with the composition according to the invention.

TECHNICAL BACKGROUND

Hereinbelow, the invention is presented in relation with catheter balloons, the problems specific thereto and their functionalities, but it is clearly understood that the composition according to the invention is capable of satisfying the technical requirements of other parts of a catheter, especially the stem.

Cuffed expansion catheters are used in percutaneous transluminal coronary angioplasty (PTCA), which is a process that is widely used for treating coronary disease. In the PTCA procedure, a cuffed expansion catheter is advanced in a patient's coronary artery and the catheter cuff is inflated inside the stenosed region of the patient's artery to open the arterial passage and thus increase the blood flow. Generally, the shape and diameter of the inflated cuff are predetermined and correspond approximately to the original diameter of the lumen of the normally dilated artery, so as to dilate the artery but without further widening its wall. Once the cuff has been deflated, the blood flow in the artery thus dilated then resumes and the expansion catheter may be removed therefrom.

To prevent the restenosis rate and to reinforce the space thus expanded, doctors often implant an intravascular prosthesis, generally known as a stent, inside the artery at the site of the lesion. Stents may also be used for repairing vessels or reinforcing a weakened section of a vessel. Stents are generally placed in the desired position inside a contracted or shrunken coronary artery, by means of a catheter balloon similar to an angioplasty catheter balloon, and widened to a larger diameter by expanding the balloon. The balloon is then deflated to remove the catheter and the stent is positioned in the artery at the thus-expanded site of the lesion.

The expansion catheter balloons of the prior art, generally used in angioplasty procedures, are formed from inelastic polymer materials such as polyvinyl chloride (PVC), polyethylene (PE), polyethylene terephthalate (PET), polyolefinic ionomers, and polyamide (PA). One advantage of these inelastic materials, when they are used in catheter balloons, is that the tensile strength, and consequently the mean breaking pressure, of the balloon is high.

Specifically, catheter balloons must have a high tensile strength so as to exert a sufficient pressure on the stenosed vessel to efficiently open the patient's circulation. Furthermore, a high-tensile balloon may be inflated to high pressures without any risk of the balloon bursting during pressurization. Finally, the wall thickness of a high-strength balloon may be reduced, so as to decrease the profile of the catheter without the risk of bursting. Specifically, there is a direct relationship between the bursting pressure and the tensile stress (see in this respect the article "Medical Device and Diagnostic Industry: New extrusion techniques advance catheter design", by Byron Flagg (Putnam Plastics), http://www.mddionline.com/article/new-extrusion-techniques-advance-catheter-design).

The drawback of these inelastic materials having the least elasticity is their lack of "compliance". Specifically, these materials are classified as "non-compliant" materials and "semi-compliant" materials, and especially include PET and polyamide. The non-compliant material shows little expansion in response to increasing levels of inflation pressure. For these non-compliant materials, on account of the limited capacity of the balloon to increase its diameter, the inflated balloon must be sufficiently large so that, once inflated, the balloon has a working diameter that is sufficient to compress the stenosis and open the patient's circulation. However, a large-profile non-compliant balloon may make the catheter difficult to advance in the patient's narrow vascular system since, in an uninflated state, these balloons form flat-shaped wings (like a pancake) which extend radially outward. Consequently, the aim of the present invention is to provide a catheter balloon material that has better compliance. Balloons formed from compliant materials have increased flexibility, which improves the capacity of the probe to follow the patient's sinuous vascular system and to pass through the stenosis, and allows the cuff to be correctly positioned at the site of the stenosis. The flexibility of a balloon is expressed by the flexural modulus of elasticity of the cuff. A relatively flexible (or soft) balloon has a relatively low flexural modulus of elasticity, i.e. below about 1000 MPa.

Other polymer materials, in particular copolymers containing polyamide blocks and polyether blocks (PEBA), are used in the manufacture of catheters to improve their glidant aspect and thus to allow more comfortable insertion into a patient's vessels. PEBAs may also be used for manufacturing catheter balloons, and these materials, which have advantageous properties of high tensile strength, high elongation and low flexural modulus, make it possible partly to satisfy the abovementioned requirements.

The compliance of the PEBA materials currently used is marked by a stress (MPa)—strain (%) curve, the profile of which is characterized by a first "compliant" segment, which is generally linear, and a second "non-compliant" segment (not following a linear strain), separated by a transition segment corresponding to the threshold of the stress-strain curve.

It turns out that PEBA balloons often have a nonuniform wall thickness, which is unacceptable for catheter applications on account of the risks of bursting during their inflation.

The aim of the present invention is thus to provide a process for improving and facilitating the manufacture of PEBA-based balloons or cuffs, so that they have the most uniform possible wall thickness. This property is desirable to limit the risks of bursting during their inflation, whether it be during their manufacture or during their use.

The present invention is directed in particular toward providing "compliant" materials, allowing better control of the uniformity of the wall thickness of the catheter balloon, and thus reducing the amount of rejected balloons. The aim of the present invention is also to manufacture balloons or cuffs with walls that are as thin as possible, making it possible both to use balloon catheters that are as uninvasive as possible during their insertion into vessels, and to improve the safety of use of these balloons by limiting their risk of bursting, while at the same time using less polymer starting material.

The Applicant has now found that a special choice of PEBA, having a particular profile curve, makes it possible to readily control the uniformity of the wall thickness of the balloon during its manufacture. Surprisingly, certain PEBA materials which have a compliance curve whose intermediate segment is as short as possible or even nonexistent between the compliant segment and the non-compliant segment, make it possible to readily manufacture balloons of uniform wall thickness. The term "uniform wall thickness" means a wall that has the same thickness over its entire surface.

BRIEF DESCRIPTION OF THE DRAWINGS

FIG. 1 compares stress-strain curves for specimens using the "long-block" PEBAs of the invention (ex. 1 and ex. 2), to similar structures using the "short-block" PEBAs of the prior art.

DESCRIPTION OF THE INVENTION

This is accomplished by means of the use according to the invention of copolymers containing polyether blocks and polyamide blocks known as "long blocks" according to the invention, as defined below according to the number-average molecular mass of the PA and PE blocks.

One subject of the present invention is thus the use of a copolymer containing polyether blocks and polyamide blocks for manufacturing an inflatable catheter element, such as a catheter balloon, with improved bursting strength, in which said copolymer has the following characteristics:
number-average molecular mass of the PE blocks of greater than 500 g/mol,
number-average molecular mass of the PA blocks of greater than 10 000 g/mol.

This result is particularly surprising insofar as long-block elastomeric thermoplastic polymers are generally much more difficult to synthesize due to the greater incompatibility of the blocks as a function of their length—the longer the polymer chains, more precisely in the present case PE and PA, the more they will be incompatible—and difficult to process without presenting appreciable advantages over conventional short-block elastomers.

Contrary to the general teaching of a person skilled in the art, the inventors have noted that the presence of these particularly long PA and PE blocks makes it possible to improve the bursting strength, and also the stiffness, for equivalent molecular masses without any impact regarding the processing.

The present invention makes it possible to overcome the drawbacks of the prior art by using a particular type of elastomeric thermoplastic polymers, for the manufacture of materials comprising the three qualities required for use in catheter balloons: flexibility, bursting strength and "compliance", as defined below:
flexibility, i.e. the flexural modulus of elasticity, less than 1000 MPa and greater than 525 MPa, measured according to international standard ISO 178;
bursting strength, in particular the tensile strength, i.e. of threshold stress greater than 20 MPa and of threshold strain greater than 22%, measured according to standard ISO 527; and
"compliance", i.e. for which the difference between the threshold stress and the strain at the flow plateau is less than 0.5 MPa, and for which the ratio between the threshold strain and the strain at the flow plateau is greater than 0.5, the stresses and strains being measured according to standard ISO 527.

As regards amide block copolyethers, also known as copolymers containing polyether blocks and polyamide blocks, abbreviated as "PEBA", they result from the polycondensation of polyamide blocks bearing reactive end groups with polyether blocks bearing reactive end groups, such as, inter alia:

1) polyamide blocks bearing diamine chain ends with polyoxyalkylene blocks bearing dicarboxylic chain ends;

2) polyamide blocks bearing dicarboxylic chain ends with polyoxyalkylene blocks bearing diamine chain ends, obtained by cyanoethylation and hydrogenation of aliphatic alpha-omega dihydroxylated polyoxyalkylene blocks known as polyetherdiols;

3) polyamide blocks bearing dicarboxylic chain ends with polyetherdiols, the products obtained being, in this particular case, polyetheresteramides.

The polyamide blocks bearing dicarboxylic chain ends originate, for example, from the condensation of polyamide precursors in the presence of a chain-limiting dicarboxylic acid. The polyamide blocks bearing diamine chain ends originate, for example, from the condensation of polyamide precursors in the presence of a chain-limiting diamine.

The polymers containing polyamide blocks and polyether blocks may also comprise randomly distributed units.

Three types of polyamide blocks may advantageously be used.

According to a first type, the polyamide blocks originate from the condensation of a dicarboxylic acid, in particular those containing from 4 to 20 carbon atoms, preferably those containing from 6 to 18 carbon atoms, and of an aliphatic or aromatic diamine, in particular those containing from 2 to 20 carbon atoms, preferably those containing from 6 to 14 carbon atoms.

Examples of dicarboxylic acids that may be mentioned include 1,4-cyclohexyldicarboxylic acid, butanedioic acid, adipic acid, azelaic acid, suberic acid, sebacic acid, dodecanedicarboxylic acid, octadecanedicarboxylic acid and terephthalic and isophthalic acid, but also dimerized fatty acids.

Examples of diamines that may be mentioned include tetramethylenediamine, hexamethylenediamine, 1,10-decamethylenediamine, dodecamethylenediamine, trimethylhexamethylenediamine, bis(4-aminocyclohexyl)methane (BACM), bis(3-methyl-4-aminocyclohexyl)methane (BMACM) and 2-2-bis(3-methyl-4-aminocyclohexyl)propane (BMACP) isomers, and para-aminodicyclohexylmethane (PACM), and isophoronediamine (IPDA), 2,6-bis(aminomethyl)norbornane (BAMN) and piperazine (Pip).

Advantageously, PA4.12, PA4.14, PA4.18, PA6.10, PA6.12, PA6.14, PA6.18, PA9.12, PA10.10, PA10.12, PA10.14 and PA10.18 blocks are present.

According to a second type, the polyamide blocks result from the condensation of one or more alpha,omega-aminocarboxylic acids and/or one or more lactams containing from 6 to 12 carbon atoms in the presence of a dicarboxylic acid containing from 4 to 12 carbon atoms or a diamine. Examples of lactams that may be mentioned include caprolactam, oenantholactam and lauryllactam. Examples of alpha,omega-aminocarboxylic acids that may be mentioned include aminocaproic acid, 7-aminoheptanoic acid, 11-aminoundecanoic acid and 12-aminododecanoic acid.

Advantageously, the polyamide blocks of the second type are made of polyamide 11, polyamide 12 or polyamide 6.

According to a third type, the polyamide blocks result from the condensation of at least one alpha,omega-aminocarboxylic acid (or a lactam), at least one diamine and at least one dicarboxylic acid.

In this case, the polyamide blocks PA are prepared by polycondensation:
of the linear aliphatic or aromatic diamine(s) containing X carbon atoms;
of the dicarboxylic acid(s) containing Y carbon atoms; and
of the comonomer(s) {Z}, chosen from lactams and alpha,omega-aminocarboxylic acids containing Z carbon atoms and equimolar mixtures of at least one diamine containing X1 carbon atoms and of at least one dicarboxylic acid containing Y1 carbon atoms, (X1, Y1) being different from (X, Y);
said comonomer(s) {Z} being introduced in a weight proportion ranging up to 50%, preferably up to 20%, even more advantageously up to 10% relative to all of the polyamide precursor monomers;
in the presence of a chain limiter chosen from dicarboxylic acids.

Advantageously, the dicarboxylic acid containing Y carbon atoms is used as chain limiter, which is introduced in excess relative to the stoichiometry of the diamine(s).

According to a variant of this third type, the polyamide blocks result from the condensation of at least two alpha, omega-aminocarboxylic acids or of at least two lactams containing from 6 to 12 carbon atoms or of a lactam and an aminocarboxylic acid not having the same number of carbon atoms, in the optional presence of a chain limiter. Examples of aliphatic alpha,omega-aminocarboxylic acids that may be mentioned include aminocaproic acid, 7-aminoheptanoic acid, 11-aminoundecanoic acid and 12-aminododecanoic acid. Examples of lactams that may be mentioned include caprolactam, oenantholactam and lauryllactam. Examples of aliphatic diamines that may be mentioned include hexamethylenediamine, dodecamethylenediamine and trimethylhexamethylenediamine. An example of a cycloaliphatic diacid that may be mentioned is 1,4-cyclohexyldicarboxylic acid. Examples of aliphatic diacids that may be mentioned include butanedioic acid, adipic acid, azelaic acid, suberic acid, sebacic acid, dodecanedicarboxylic acid, dimerized fatty acids (these dimerized fatty acids preferably have a dimer content of at least 98%; they are preferably hydrogenated; they are sold under the brand name Pripol® by the company Unichema, or under the brand name Empol® by the company Henkel) and α,ω-polyalkylene diacids. Examples of aromatic diacids that may be mentioned include terephthalic acid (T) and isophthalic acid (I). Examples of cycloaliphatic diamines that may be mentioned include bis(4-aminocyclohexyl)methane (BACM), bis(3-methyl-4-aminocyclohexyl)methane (BMACM) and 2-2-bis(3-methyl-4-aminocyclohexyl)propane (BMACP) isomers, and para-aminodicyclohexylmethane (PACM). The other diamines commonly used may be isophoronediamine (IPDA), 2,6-bis(aminomethyl)norbornane (BAMN) and piperazine.

As examples of polyamide blocks of the third type, mention may be made of the following:
6.6/6 in which 6.6 denotes hexamethylenediamine units condensed with adipic acid. 6 denotes units resulting from the condensation of caprolactam;
6.6/6.10/11/12 in which 6.6 denotes hexamethylenediamine condensed with adipic acid. 6.10 denotes hexamethylenediamine condensed with sebacic acid. 11 denotes units resulting from the condensation of aminoundecanoic acid. 12 denotes units resulting from the condensation of lauryllactam.

The polyamide segments may also comprise aromatic polyamides, but, in this case, significantly poorer compliance characteristics are to be expected.

The polyether blocks are constituted of alkylene oxide units. These units may be, for example, ethylene oxide units, propylene oxide units or tetrahydrofuran units (which leads to polytetramethylene glycol sequences). Use is thus made of PEG (polyethylene glycol) blocks, i.e. those constituted of ethylene oxide units, PPG (propylene glycol) blocks, i.e. those constituted of propylene oxide units, PO3G (polytrimethylene glycol) blocks, i.e. those constituted of polytrimethylene glycol ether units (such copolymers with polytrimethylene ether blocks are described in U.S. Pat. No. 6,590, 065), and PTMG blocks, i.e. those constituted of tetramethylene glycol units also known as polytetrahydrofuran. The PEBA copolymers may comprise in their chain several types of polyethers, copolyethers which may be in block or random form. Use may also be made of blocks obtained by oxyethylation of bisphenols, for instance bisphenol A. The latter products are described in patent EP 613919.

The polyether blocks may also be constituted of ethoxylated primary amines. Examples of ethoxylated primary amines that may be mentioned include the products of formula:

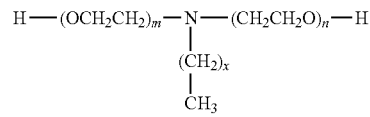

in which m and n are between 1 and 20 and x is between 8 and 18. These products are commercially available under the brand name Noramox® from the company CECA and under the brand name Genamin® from the company Clariant.

The flexible polyether blocks may comprise polyoxyalkylene blocks bearing NH2 chain ends, such blocks possibly being obtained by cyanoacetylation of aliphatic alpha-omega dihydroxylated polyoxyalkylene blocks known as polyetherdiols. More particularly, use may be made of the Jeffamine products (for example Jeffamine® D400, D2000, ED 2003 and XTJ 542, which are products sold by the company Huntsman, also described in patents JP2004346274, JP2004352794 and EP1482011).

The polyetherdiol blocks are either used as obtained and copolycondensed with polyamide blocks bearing carboxylic end groups, or they are aminated to be converted into polyetherdiamines and condensed with polyamide blocks bearing carboxylic groups. The general method for preparing in two steps PEBA copolymers with ester bonds between the PA blocks and the PE blocks is known and is described, for example, in French patent FR 2 846 332. The general method for preparing the PEBA copolymers of the invention bearing amide bonds between the PA blocks and the PE blocks is known and described, for example, in European patent EP 1 482 011. The polyether blocks may also be mixed with polyamide precursors and a diacid chain limiter to make the polymers containing polyamide blocks and polyether blocks having randomly distributed units (one-step process).

Needless to say, the name PEBA in the present description of the invention refers equally to the Pebax® products sold by Arkema, to the Vestamid® products sold by Evonik®, to the Grilamid® products sold by EMS, to the Kellaflex® products sold by DSM or any other PEBA from other suppliers.

Advantageously, the PEBA copolymers contain PA blocks made of PA 6, PA 11, PA 12, PA 6.12, PA 6.6/6, PA 10.10 and/or PA 6.14, preferably PA 11 and/or PA 12 blocks; and PE blocks made of PTMG, PPG and/or PO3G. The PEBAs based on PE blocks constituted predominantly of PEG are to be categorized in the range of hydrophilic PEBAs. The PEBAs based on PE blocks predominantly constituted of PTMG are to be categorized in the range of hydrophilic PEBAs.

Advantageously, said PEBA used in the composition according to the invention is at least partly obtained from biosourced starting materials.

The term "starting materials of renewable origin" or "biosourced starting materials" means materials which comprise biosourced carbon or carbon of renewable origin. Specifically, unlike materials derived from fossil matter, materials composed of renewable starting materials contain $^{14}C$. The "content of carbon renewable origin" or "content of biosourced carbon" is determined by applying the standards ASTM D 6866 (ASTM D 6866-06) and ASTM D 7026 (ASTM D 7026-04). By way of example, the PEBAs based on polyamide 11 at least partly originate from biosourced starting materials and have a content of biosourced carbon of at least 1%, which corresponds to a $^{12}C/^{14}C$ isotope ratio of at least $1.2 \times 10^{14}$. Preferably, the PEBAs according to the invention comprise at least 50% by mass of biosourced carbon relative to the total mass of carbon, which corresponds to a $^{12}C/^{14}C$ isotope ratio of at least $0.6 \times 10^{-12}$. This content is advantageously higher, especially up to 100%, which corresponds to a $^{12}C/^{14}C$ isotope ratio of $1.2 \times 10^{-12}$, in the case of PEBA containing PA 11 blocks and PE blocks comprising PO3G, PTMG and/or PPG derived from starting materials of renewable origin.

Advantageously, said PE blocks represent 1-20% of weight, preferably 1-10% by weight, relative to the total weight of the copolymer, and said PA blocks represent 80-99% by weight, preferably 90-99% by weight, relative to the total weight of the copolymer.

Advantageously the Shore D hardness (according to the international standard ISO 868) of the copolymer is greater than or equal to 72, preferably within the range from 72 to 76.

The weight ratio of the polyamide to the polyether in the PEBA used in the invention is between 9 and 50, preferably greater than 15.

Advantageously, the number-average molecular mass of the PE blocks is greater than 600 g/mol, preferably within the range of 600 to 2000 g/mol, preferably from 650 to 1000 g/mol.

Advantageously, the number-average molecular mass of the PA blocks is within the range from 12 000 to 32 000 g/mol, preferably from 13 000 to 25 000 g/mol. This molecular mass range is chosen so as to satisfy the maintenance of the desired flexibility levels for the composition according to the invention. The inherent viscosities of these polymers according to the invention are greater than 1.5.

Advantageously, the flexural modulus of elasticity of the copolymer (measured according to standard ISO 178) is greater than 525 MPa. The flexural modulus of elasticity of the copolymer is preferably within the range from 600 to 900 MPa. These value ranges for the flexural modulus of elasticity of the copolymer are chosen such that they are particularly suitable, firstly, for permitting the advance of the catheter in the arteries, and, secondly, for permitting the deployment of the stent associated with the catheter during the inflation of the balloon for the positioning of said stent in its dedicated site.

Advantageously, the PA blocks are formed from at least one monomer chosen from: 6, 11, 12, 4.6, 4.12, 4.14, 4.18, 6.6, 6.10, 6.12, 6.14, 6.18, Pip.10, 9.6, 9.12, 10.10, 10.12, 10.14, 10.18, 10.36, 10.T, 6.T, 9.T, MXD.6, MXD.10, B.10, B.12, B.14, B.18, B.36, P.10, P.12, P.14, P.18, P.36, random and/or block copolymers thereof, and mixtures thereof.

Advantageously, said at least one PE block of the copolymer used in the invention comprises at least one polyether chosen from polyalkylene ether polyols, such as PEG, PPG, PO3G, PTMG, polyethers containing polyoxyalkylene sequences bearing NH2 groups at the chain ends, random and/or block copolymers thereof and mixtures thereof.

Preferably, the copolymer comprises polyether blocks predominantly composed of PTMG, preferably solely composed of PTMG.

A subject of the present invention is also a polyamide-based thermoplastic polymer composition, said composition comprising:
from 30% to 100% by weight of copolymer in accordance with the invention,
from 0 to 70% by weight of at least one other polymer chosen from polyamides, PEBAs other than those used according to the invention, TPU, COPE, PVC, ABS, PS, PET, PETE, PVDF, ETFE, Polyimide, PEEK, PEKK, silicone, "silicone rubber",
from 0 to 40% of additive, relative to the total weight of the composition.

In the conventional case, it should be noted that the additives are not present to more than 20% in the composition according to the invention. Nevertheless, in the event in particular that functional additives (tracers) of the $Ba_2SO_4$ (barium sulfate) and/or WC (tungsten carbide) type are used, the amount of additives may be greater than 20% by weight of the composition.

Preferably, the additive is chosen from coloring agents, especially pigments, dyes, pigments with an effect, such as defracting pigments, interference pigments, such as nacres, reflective pigments and mixtures thereof; UV stabilizers, antiaging agents, antioxidants; fluidizers, antiabrasion agents, mold-release agents, stabilizers; plasticizers, impact modifiers; surfactants; optical brighteners; fillers, such as silica, carbon black, carbon nanotubes, expanded graphite, titanium oxide or glass beads; fibers; waxes; and mixtures thereof. Functional additives serving as antimicrobial or bactericidal agents or laser markers may also be envisaged.

The composition as defined above may advantageously be used for constituting granules or powders.

Said granules are used especially for making a burst-proof inflatable catheter balloon.

Another subject of the present invention is a process for manufacturing a burst-proof catheter balloon, said process comprising:
a step of providing copolymer in accordance with that defined in any one of claims 1 to 9;
an optional step of mixing said copolymer with at least one other polymer and/or at least one additive, so as to manufacture a composition as defined in claim 10;
a step of processing said copolymer or said composition at a temperature T0 within the range from 200 to 300° C.;
a step of forming the balloon at a temperature below the Tm (melting point) of the copolymer;
a step of recovering the balloon.

Advantageously, the process according to the invention comprises at least one of the following steps: "dry blending", extrusion, especially coextrusion, tube extrusion, overmolding, blow-molding, and mixtures thereof.

According to a particular embodiment the PEBA in accordance with the invention is used for manufacturing the catheter stem and a catheter balloon comprising one or more layers of composition as defined above.

In a preferred embodiment, the balloon is formed from a single polymer layer formed at least partly from "long-block" PEBA according to the invention. However, the balloon may also comprise several layers, at least one of which is a layer at least partly constituted of PEBA according to the invention.

The preferred balloon is formed from 100% PEBA according to the invention. However, the balloon may be formed from a mixture of PEBA with one or more different polymer materials. The polymer materials that are suitable for mixing with "long-block" PEBAs according to the invention comprise the polymers listed previously, commonly used for manufacturing expansion catheter balloons, such as polyamide or "short-block" PEBA not in accordance with the invention.

The preferred polymer mixture is a mixture of PEBA according to the invention and of polyamide, in which the preferred weight percentage of polyamide is within the range from 30% to 95% of the total weight. The preferred polyamide is polyamide 11, polyamide 12 or mixtures thereof.

In the case of a balloon comprising several layers formed by coextrusion, the PEBA according to the invention may be the inner layer or the outer layer of the balloon.

One subject of the present invention is thus an inflatable element, especially a burst-proof catheter balloon or cuff, having a composition in accordance with the invention, i.e. formed at least partly from the particular range of copolymers containing polyether blocks and polyamide blocks (PEBA) selected according to the invention.

The balloon according to the invention advantageously has a wall thickness within the range from 1 to 250 µm, preferably from 2 to 60 µm, preferably from 3 to 50 µm, preferably from 4 to 40 µm.

A subject of the present invention is also a catheter comprising a balloon in accordance with that defined previously.

Various models of cuffed catheters that are well known in the field may be used as balloon catheter according to the invention formed at least partly from PEBA. The cuffed catheter according to the invention comprises, for example, a catheter having an elongated shaft and an inflatable balloon formed at least partly from "long-block" PEBA according to the invention on a distal part of the catheter.

For example, the catheter may be a standard expansion catheter for angioplasty. In addition, the catheter may be used for posing a stent, first mounted on the cuff of the catheter.

The PEBA-based balloon according to the invention, comprising improved flexibility and improved tensile strength makes it possible to provide balloon catheters of thin profile, having an excellent capacity to be inserted into the pathways of a patient's vascular system, to pass through the stenosis and to compress the stenosis in order to open the patient's blood vessel.

The balloon of the invention may be produced via standard techniques for manufacturing inflatable catheter elements, such as blow-molding, and may be preformed by drawing a straight tube before the balloon is blown. The balloons may be formed by tube expansion, for example in a circle ratio of between 3 and 8. The bonding of the cuff to the catheter may be performed via standard techniques, such as those using adhesives and/or by fusion, optionally with compatibilizers. The cuff may be inflated with a radio-opaque fluid via an inflation orifice located in the catheter stem, or by other means, especially via a passage formed between the exterior of the catheter stem and the element forming the balloon, as a function of the particular design of the catheter. The details and mechanisms for inflating the cuff vary as a function of the particular design of the catheter, and are well known to a person skilled in the art in the field of catheters. The length of the cuff can be about 0.5 cm to about 6 cm, preferably from about 1.0 cm to about 4.0 cm. After having been formed, the cuff has, for example, an outside diameter at the nominal pressure (for example 6-8 atm) from about 0.15 cm to about 0.4 cm, and typically about 0.3 cm, but balloons with an outside diameter of about 1 cm may also be used. The single wall thickness is within the range from 1 to 250 µm, preferably from 2 to 60 µm, preferably from 3 to 50 µm, preferably from 4 to 40 µm, for example from about 10 µm to about 40 µm, and generally 15 µm. In the embodiment in which the cuff derived from coextrusion comprises two layers, the PA layer preferably has a single wall thickness of from 5 to 15 µm, and the PEBA layer preferably has a thickness ranging from 2 to 12 µm.

According to another embodiment of the invention, a stent is placed around the balloon for insertion inside a patient's vessel. For example, the stent material may be made of stainless steel, an NiTi alloy, a plastic material or other materials. The stent has a diameter that is small enough to allow its insertion and advance in the patient's vessels, and can be expanded to a larger diameter for implantation into the patient's lumens. The balloon according to the invention formed at least partly from PEBA has, by virtue of the "long-block" PEBA according to the invention, better glidance, which is useful for inserting a stent. In the embodiment of the invention in which the cuff has at least two coextruded layers, a cuff used for inserting a stent preferably has the PEBA layer as single outer layer, for providing better glidance during the insertion of the vascular endoprothesis. In addition, the retention force of the stent is improved when the cuff is formed by coextrusion.

EXAMPLES

The examples below illustrate the present invention without limiting its scope. In the examples, unless otherwise stated, all the percentages and parts are expressed on a weight basis.

In table 1 below and in the graph of FIG. 1, the stress and strain properties are measured in a uniaxial tensile test on injected specimens ISO 527 1A, test conditions: 45° C., piston travel speed V=50 mm/minute (according to standard ISO 527, Zwick 3, optical extensometer).

TABLE 1

|  | Size of the PA12- PTMG blocks (g/mol) of the PEBA | Inherent viscosity | Shore D hardness (ISO 868) | Threshold strain % | Threshold stress (MPa) | Strain at the flow plateau (%) | Stress at the flow plateau (MPa) | Stress at 100% strain (MPa) |
|---|---|---|---|---|---|---|---|---|
| Ex 1 | 14000 - 650 | 1.53 | 74 | 25.8 | 22.8 | 40 | 22.7 | 24.4 |
| Ex 2 | 14000 - 650 | 1.53 | 72 | 23.8 | 21.9 | 40 | 21.4 | 22.6 |
| Cp 1 | 5000 - 250 | 1.38 | 72 | 21.8 | 20 | 55 | 19.3 | 20 |

In table 2 below, flexural modulus of elasticity is measured at 23° C. (conditioned sample). The standard used here is international standard ISO 178, the measuring machine consists of a Zwick 1465, 2 mm/min, displacement sensor.

TABLE 2

|  | Size of the PA12 - PTMG blocks of the PEBA | Flexural modulus of elasticity at 23° C. (MPa) |
|---|---|---|
| Ex 1 | 14 000 g/mol - 650 g/mol | 625 |
| Ex 2 | 14 000 g/mol - 650 g/mol | 700 |
| Cp 1 | 5000 g/mol - 250 g/mol | 525 |

The graph in FIG. 1 and tables 1 and 2 show that the catheter balloons using the "long-block" PEBAs in accordance with the invention (ex. 1 and ex. 2) have several advantageous mechanical properties when compared with similar structures using the "short-block" PEBAs of the prior art (Cp 1):
  higher modulus of elasticity;
  better tensile strength, thus higher bursting pressure measured by a higher threshold stress and threshold strain;
  improved "compliance" marked by:
  "less pronounced softening", i.e. smaller differences between the threshold stress and threshold strain and the stress and strain at the flow plateau; and also by
  greater hardening under stress (or rheohardening), represented by the increase in stress with strain after the plasticity threshold, i.e. by comparing the threshold stress and the stress at 100% strain. The plasticity threshold was measured according to standard ISO 527:1 (highest data point in the flow threshold region).

In conclusion, it is clearly confirmed that the PEBA material according to the invention is:
  burst-proof, in particular resistant to tensile stress, i.e. with a threshold stress of greater than 20 MPa and at threshold strain of greater than 22%, measured according to ISO 527, and
  "compliant", i.e. for which the difference between the threshold stress and the stress at the flow plateau is less than 0.5 MPa, and for which the ratio between the threshold strain and the strain at the flow plateau is greater than 0.5, the stresses and strains being measured according to standard ISO 527.

The balloon according to the invention, especially that formed using the PEBAs of ex. 1 and ex. 2, has a uniform wall thickness and a tensile strength that is sufficient to withstand both the inflation pressure necessary for inflating the cuff and to compress a stenosis in a patient's vessel.

The invention claimed is:

1. A process for manufacturing a burst-proof catheter balloon, said process comprising:
  a) a step of providing a copolymer containing polyether blocks and polyamide blocks in which said copolymer has the following characteristics:
    1) number-average molecular mass of the polyether blocks greater than 500 g/mol,
    2) number-average molecular mass of the polyamide blocks greater than 13,000 g/mol, and
    3) the copolymer comprises polyether blocks composed of a majority of PTMG monomer units,
    4) a Shore hardness of greater than 72;
  b) an optional step of mixing said copolymer with at least one other polymer and/or at least one additive, so as to manufacture a composition comprising:
    1) from 30% to 100% by weight of a said copolymer containing polyether blocks and polyamide blocks
    2) from 0 to 70% by weight of at least one other polymer chosen from polyamides, TPU, COPE, PVC, ABS, PS, PET, PETE, PVDF, ETFE, Polyimide, PEEK, PEKK, and silicone,
    3) from 0 to 40% of at least one additive, relative to the total weight of the composition;
  c) a step of processing said copolymer or said composition at a temperature within the range from 200 to 300° C.;
  d) a step of forming the balloon at a temperature below the Tm (melting point) of the copolymer;
  e) a step of recovering the balloon.

2. The process as claimed in claim 1, comprising wherein said processing step c) comprises at least one of the following steps: dry blending, extrusion, coextrusion, tube extrusion, overmolding, blow-molding, and combinations thereof.

3. A method comprising manufacturing an inflatable catheter balloon with improved bursting strength with a powder or granule composition, wherein said powder or granule composition comprises:
  1) from 30% to 100% by weight of a copolymer containing polyether blocks and polyamide blocks in which said copolymer has the following characteristics:
    a) number-average molecular mass of the polyether blocks greater than 500 g/mol,
    b) number-average molecular mass of the polyamide blocks greater than 13,000 g/mol, and
    c) the copolymer comprises polyether blocks composed of a majority of PTMG monomer units,
    d) a Shore hardness of greater than 72;
  2) from 0 to 70% by weight of at least one other polymer chosen from polyamides, TPU, COPE, PVC, ABS, PS, PET, PETE, PVDF, ETFE, Polyimide, PEEK, PEKK, and silicone,
  3) from 0 to 40% of at least one additive, relative to the total weight of the composition.

* * * * *